(12) United States Patent
Li

(10) Patent No.: US 6,459,755 B1
(45) Date of Patent: Oct. 1, 2002

(54) METHOD AND APPARATUS FOR ADMINISTERING LOW DOSE CT SCANS

(75) Inventor: Jianying Li, New Berlin, WI (US)

(73) Assignee: GE Medical Systems Global Technology Co. LLC, Waukesha, WI (US)

( * ) Notice: Subject to any disclaimer, the term of this patent is extended or adjusted under 35 U.S.C. 154(b) by 0 days.

(21) Appl. No.: 09/683,873

(22) Filed: Feb. 26, 2002

(51) Int. Cl.[7] .............................. A61B 6/03; G01N 23/04
(52) U.S. Cl. ........................................... 378/4; 378/901
(58) Field of Search ............................ 378/4, 8, 15, 901

(56) References Cited

U.S. PATENT DOCUMENTS 4,149,081 A * 4/1979 Seppi ........................ 378/156
5,822,393 A * 10/1998 Popescu .................... 378/108
6,094,468 A * 7/2000 Wilting et al. ............... 378/16

* cited by examiner

Primary Examiner—David V. Bruce
(74) Attorney, Agent, or Firm—Timothy J. Ziolkowski, Esq.; Michael A. Della Penna, Esq.; Carl B. Horton, Esq.

(57) ABSTRACT

The present invention is directed to a method and apparatus for administering computed tomography (CT) imaging scans with reduced radiation dosage. The present invention includes an algorithm that allows for reduction of the sampling rate and tube current to acquire a first set of angular views. A second set of angular views is then created using interpolation from the first set of angular views. The sets of angular views are then combined to form a final set of angular views that are used to create an aliasing-free image of the scan subject. The present invention is particularly applicable for scanning centralized small objects such as the heart or the head and also is particularly useful in acquiring imaging data of pediatric patients.

20 Claims, 6 Drawing Sheets

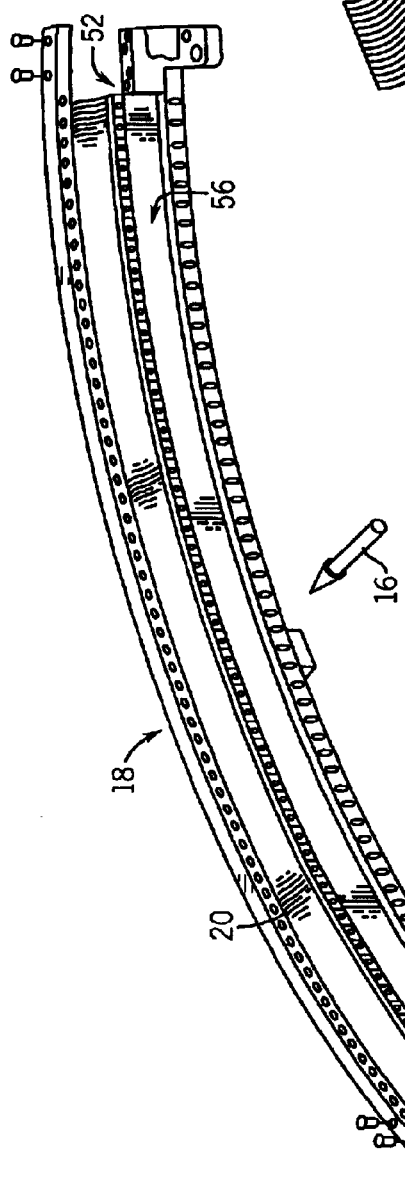
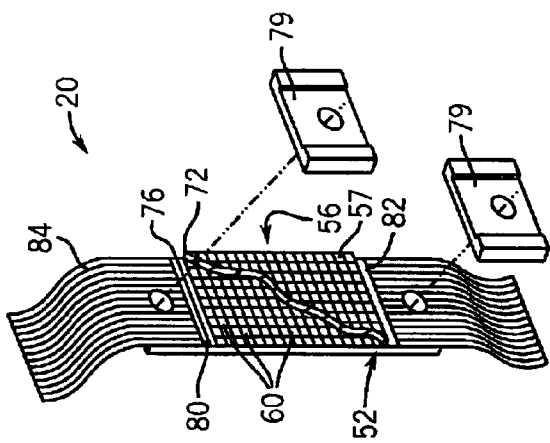
FIG. 3
FIG. 4

METHOD AND APPARATUS FOR ADMINISTERING LOW DOSE CT SCANS

BACKGROUND OF INVENTION

The present invention relates generally to computed tomography (CT) imaging and, more particularly, to a method and apparatus for administering low dose CT scans.

Typically, in computed tomography (CT) imaging systems, an x-ray source emits a fan-shaped beam toward a subject or object, such as a patient or a piece of luggage. The terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately results in the formation of an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to a data processing system.

Increasingly, there is a need for administering CT scans with reduced radiation exposure to the subject. This need is especially apparent for situations involving patient screening as well as imaging pediatric patients. Exposing a subject to be scanned such as a medical patient to radiation is necessary for acquiring CT imaging data, but limiting the radiation exposure to only that which is needed for acquiring the imaging data remains important especially for those subjects having underdeveloped immune systems such as pediatric patients.

Several techniques have been implemented to reduce radiation exposure to pediatric patients including hardware changes to the types of filters used in the CT system as well as lowering the tube current while acquiring imaging data. Hardware changes to the CT system, however, require a redundancy of imaging stations within a single treatment facility because the CT system designed for acquiring data of pediatric patients has limited applicability for acquiring data of non-pediatric subjects. Further, simply lowering the tube current while acquiring imaging data of the pediatric patient may not be sufficient to reduce the patient's exposure to unnecessary radiation. Further, simply lowering the tube current while maintaining the same data acquisition trigger frequency may introduce additional noise due to the greater contribution of the data acquisition system (DAS) noise at low signal level.

It would therefore be desirable to design a apparatus and method for acquiring imaging data of a subject with reduced radiation exposure to the subject during acquisition of the imaging data while minimizing the DAS noise impact. Further, it would also be desirable to design such a system that is applicable with known CT systems thereby eliminating the need to make changes to the hardware of the CT system.

BRIEF DESCRIPTION OF INVENTION

The present invention is directed to a method and apparatus for acquiring CT imaging data with reduced radiation dosage overcoming the aforementioned drawbacks. The present invention is particularly applicable for scanning centralized small objects such as a heart or a head as well as acquiring imaging data of pediatric patients. Further, the present invention may also be implemented in patient screening scans where slightly degraded images near the edge of the patient are acceptable.

Therefore, in accordance with one aspect of the present invention, a method prescribing a low dose scan of a subject to be scanned includes the steps of receiving a user input to lower tube current and acquiring a first set of angular views of the subject. The method further includes the steps of interpolating between each view of the first set of angular views and generating a second set of angular views therefrom. The method also includes the step of reconstructing an image of the subject from the first set and the second set of angular views.

In accordance with a further aspect of the present invention, a computer readable storage medium having a computer program stored thereon is also provided. The computer program represents a set of instructions that when executed by a computer causes the computer to reduce the tube current of a CT imaging apparatus used to acquire imaging projections of a subject. The set of instructions further causes the computer to acquire a set of imaging projections corresponding to a set of angular views of the subject. The computer program then causes the computer to determine a set of pseudo-angular views from the set of imaging projections. The set of instructions then cause the computer to combine the set of angular views and the set of pseudo-angular views into a final set of angular views. The computer is then caused to reconstruct an image of the subject from the final set of angular views.

In accordance with yet another aspect of the present invention, a CT system includes a rotatable gantry having an opening therein to receive a subject and a high frequency electromagnetic energy projection source configured to project high frequency electromagnetic energy to the subject. The CT system further includes a detector array configured to detect high frequency electromagnetic energy attenuated by the subject and generate a plurality of electrical signals indicative of the high frequency electromagnetic energy detected. The CT system further includes a computer connected to the detector array and programmed to acquire a set of projections from at least one region of the subject as well as determine a first set of views of the at least one region of the subject from the set of projections. The computer is also programmed to generate a second set of views from the first set of views and reconstruct an image of the at least one region of the subject from the first set and second set of views.

In accordance with yet another aspect of the present invention, a CT system is provided and includes means for acquiring a set of projection data from a set of angular views of a subject as well as means for generating a set of pseudo-angular views from the set of angular views. The CT system further includes a means for forming a final set of angular views from the set of angular views and set of pseudo-angular views as well as a means for reconstructing images of the subject from the final set of angular views.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a perspective view of one embodiment of a CT system detector array.

FIG. 4 is a perspective view of one embodiment of a detector.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate, that the present invention is equally applicable for the detection and conversion of other high frequency electromagnetic energy. Additionally, the present invention will be described with respect to a "third generation" CT system, but is also applicable with other CT systems.

Figure 1:
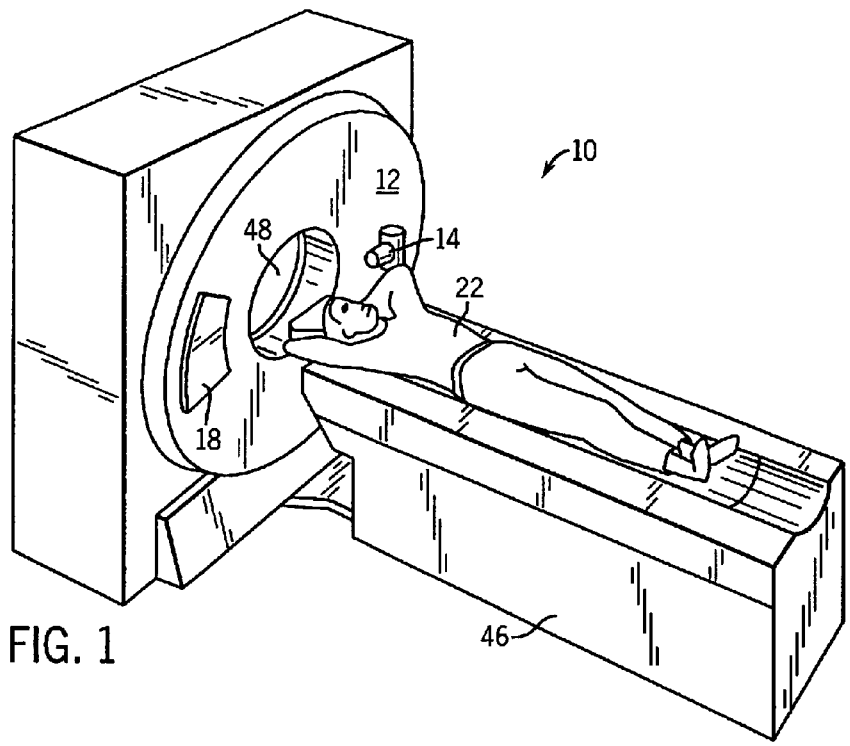
FIG. 1 is a pictorial view of a CT imaging system.
Figure 2:
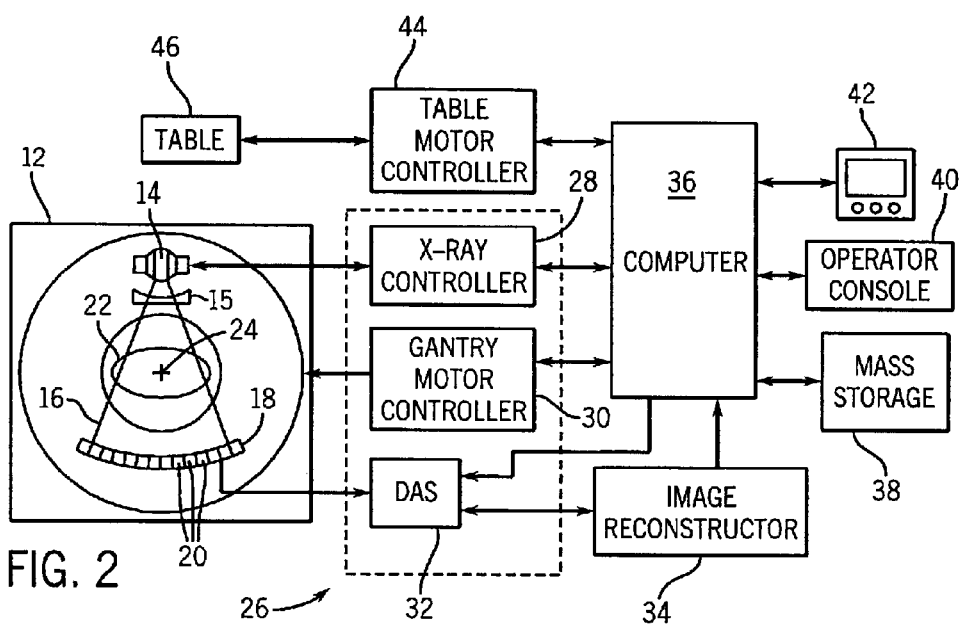
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective scintillators and a number of output leads electrically connected to DAS 32 via a flexible electrical interface 84. Particularly, about one-half of scintillator outputs are electrically connected to switch 80 with the other one-half of scintillator outputs electrically connected to switch 82. Each detector 20 is secured to a detector frame 77, FIG. 3, by mounting brackets 79.

Switch arrays 80 and 82 further include a decoder (not shown) that enables, disables, or combines scintillator outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the scintillator array 52 are activated, resulting in 16 simultaneous slices of data for processing by DAS 32. Of course, many other slice combinations are possible. For example, decoder may also select from other slice modes, including one, two, and four-slice modes.

Figure 5:
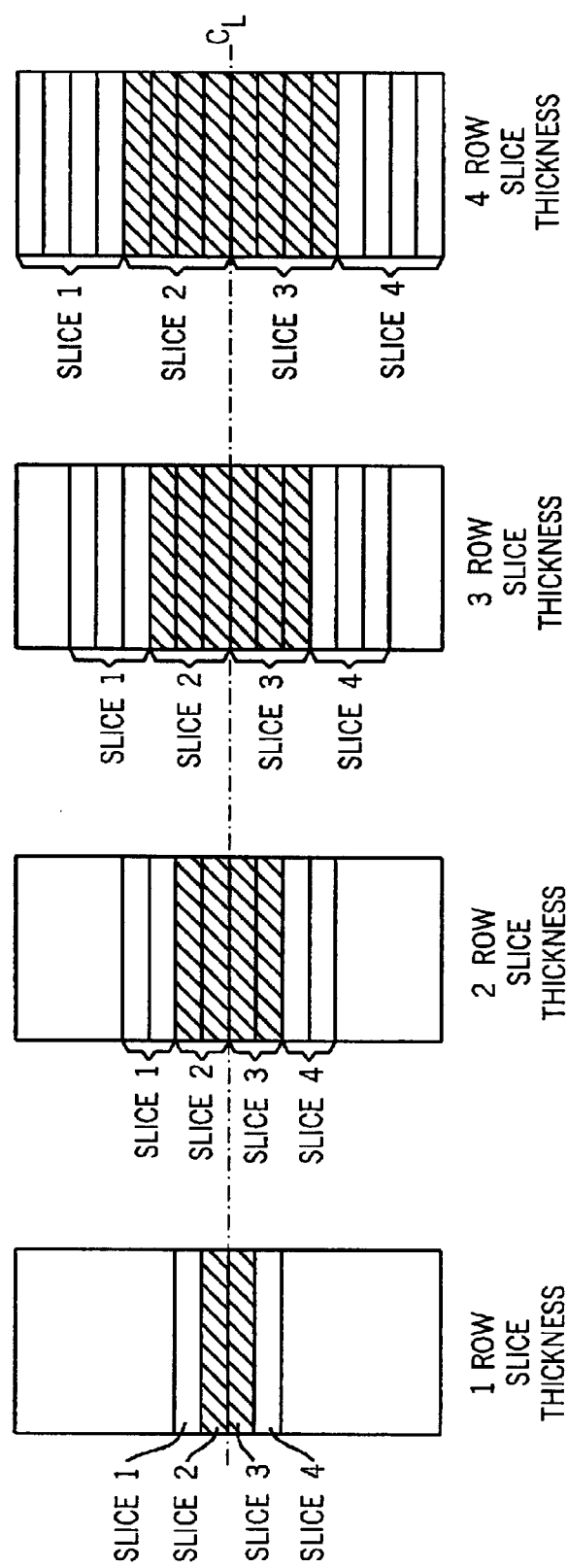
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of scintillator array 56. Depending upon the specific configuration of switch arrays 80 and 82, various combinations of scintillators 57 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

The present invention may be incorporated into a CT medical imaging device similar to that shown in FIG. 1.

Alternatively, however, the present invention may also be incorporated into a non-invasive package or baggage inspection system, such as those used by postal inspection and airport security systems.

Figure 6:
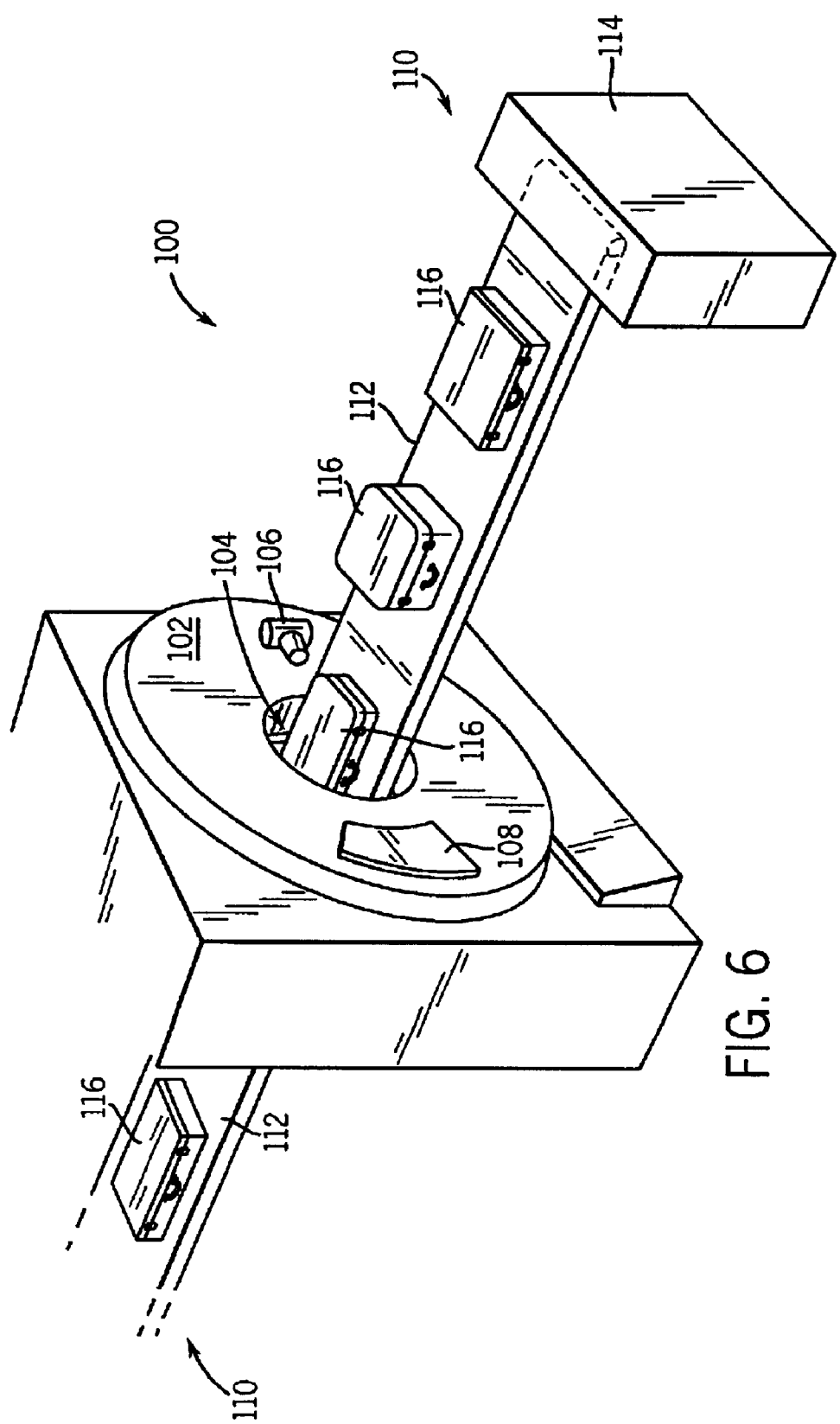
FIG. 6 is a pictorial view of a CT system for use with a non-invasive package inspection system.

Referring now to FIG. 6, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Figure 7:
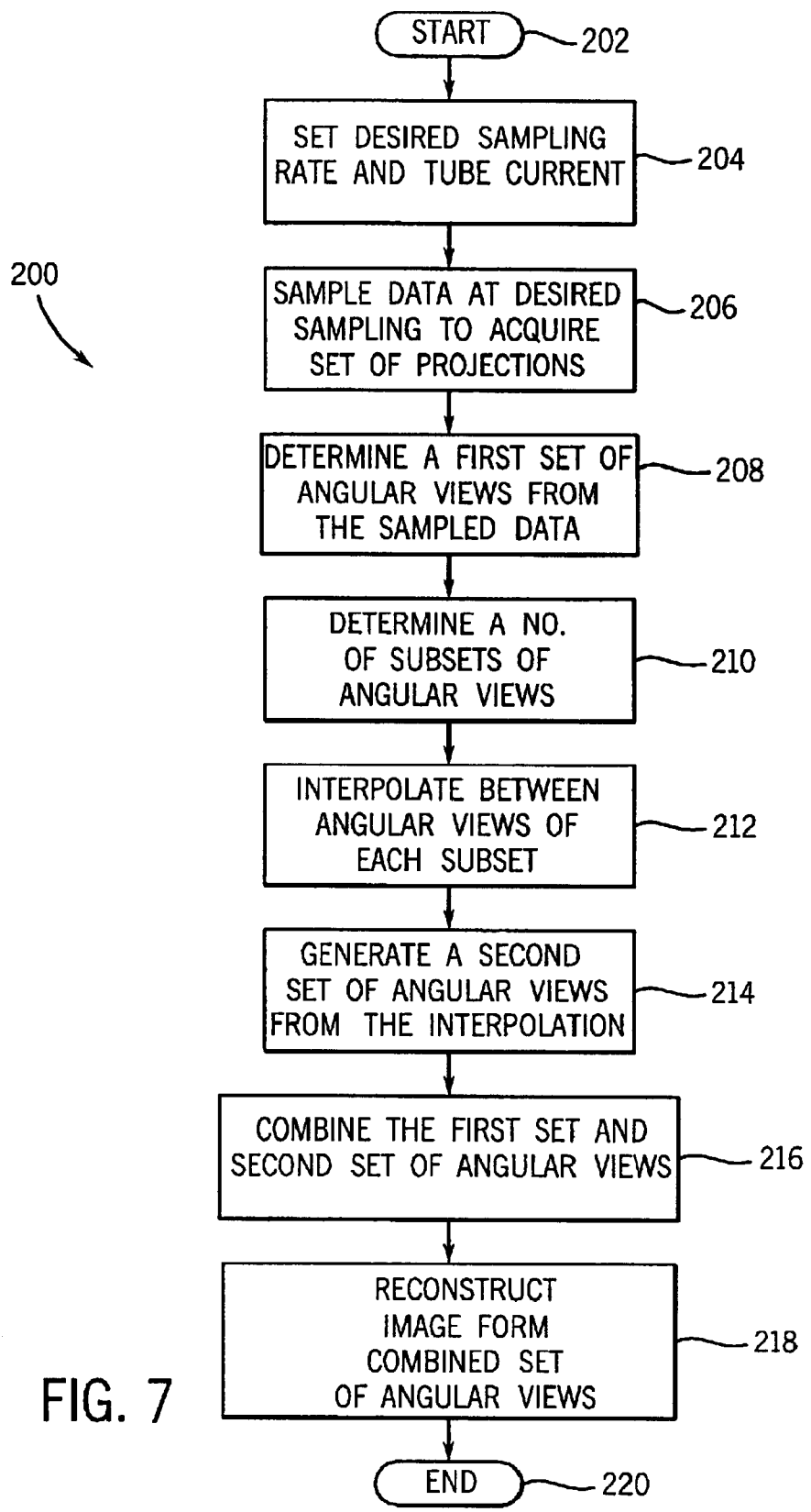
FIG. 7 is a flow chart setting forth an algorithm for administering a CT scan in accordance with the present invention.

Referring now to FIG. 7, the steps of an algorithm for administering a scan with reduced radiation dosage are set forth. The algorithm 200 begins at 202 with the user setting a desired sampling rate and tube current rate 204 for acquiring imaging data of a subject to be scanned. The subject may include a pediatric patient or a centralized small object such as a heart or a head of an adult patient. After the desired sampling rate and tube current are established 204, data is acquired of the subject to be scanned and sampled to acquire a set of projections 206. It should be noted that the trigger frequency may be less than the trigger frequency generally needed. From the set of projections, a first set of angular views is determined at 208. Because the subject to be scanned is either a small object such as a heart of a head or a body of a pediatric patient, the required number of angular views necessary to reconstruct an image may be smaller than that which is normally needed to reconstruct images for adult body scans. That is, fewer angular views are needed for image reconstruction because projection changes between adjacent views are generally small. Therefore, an adequate angular sampling may be compensated for using angular view information acquired before and after a missed angular sampling.

After a set of angular views is determined 208, the set of angular views is partitioned into a number of subsets of angular views. Preferably, each subset of angular views comprises two adjacent angular views. For example, the first subset of angular views would include a first angular and a second angular view, $\alpha_1$ and $\alpha_2$, respectively, whereas the second subset of angular views would include a third angular view, $\alpha_3$, and a fourth angular view, $\alpha_4$. Following segmenting of the angular views into a number of subsets at 210, an interpolation is completed between angular views of each subset at 212. This interpolation 212 generates a second set of angular views 214. The second set of angular views constitute a set of pseudo-angular views, $P_i \ldots P_N$. That is, the pseudo-angular views straddle the first set of angular views. The first set and the second set of angular views are then combined at 216 to create a final set of angular views that is used to reconstruct an image at 218 of the subject scanned. Algorithm 200 then concludes at 220 with the reconstruction of an image of the subject.

Figure 8:
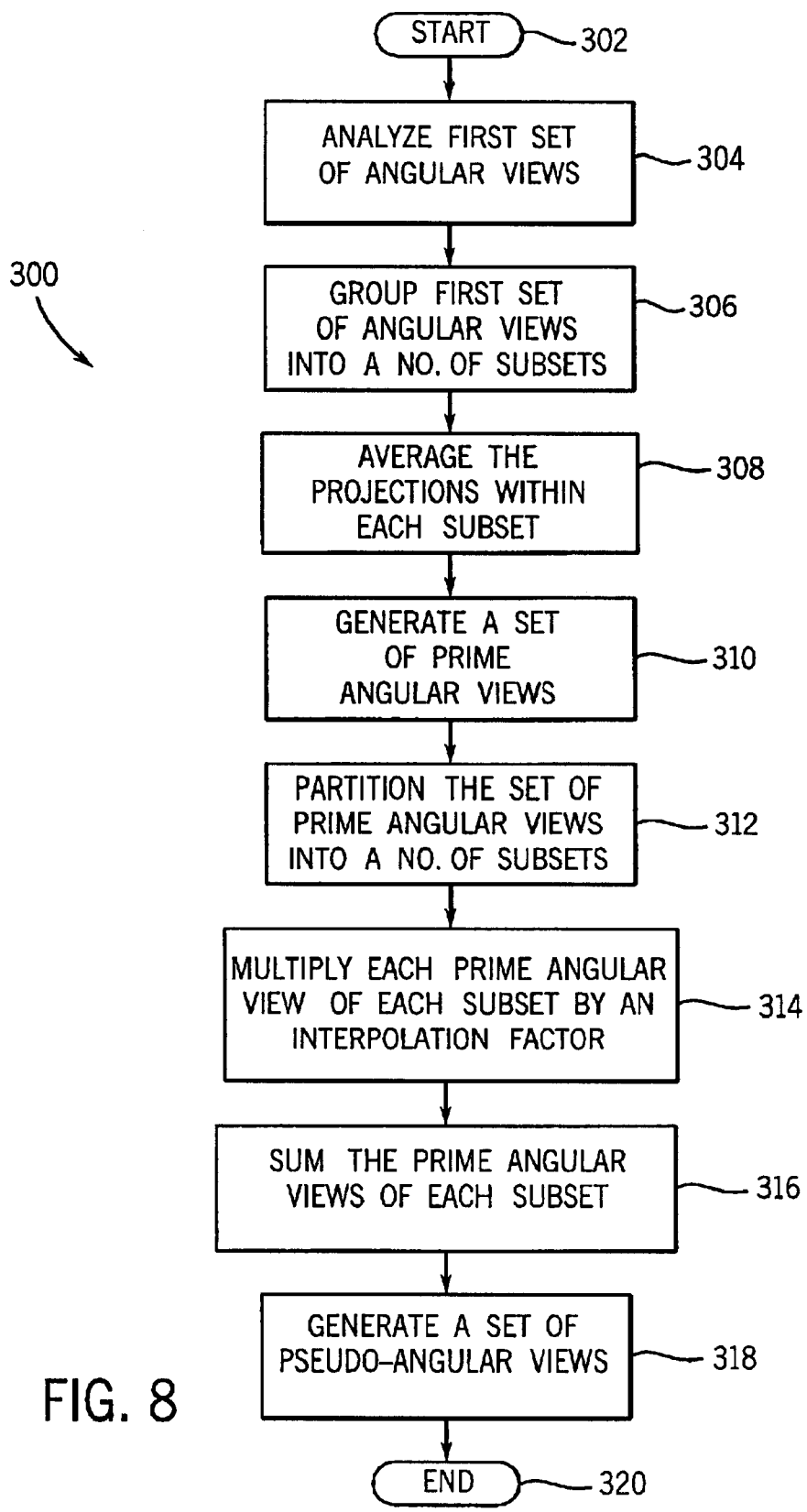
FIG. 8 is a flow chart setting forth an algorithm for generating a set of pseudo-angular views in accordance with one embodiment of the present invention.

Referring now to FIG. 8, the steps associated with an algorithm for generating the second set of angular views is set forth. The algorithm 300 begins at 302 with an analysis of the first set of angular views, $\alpha_i \ldots \alpha_N$, 304 determined at 208 of FIG. 7. The first set of angular views is then grouped into a number of subsets 306. The projections within each subset are then averaged at 308 to generate a set of prime angular views, $\alpha'_i \ldots \alpha'_N$ at 310. At 312, the set of prime angular views is partitioned into a number of subsets. That is, prime angular view 1 and prime angular view 2 are partitioned into a single subset, prime angular view 3 and prime angular view 4 are partitioned into a second subset, etc. At 314, each prime angular view of each subset is multiplied by an interpolation factor such as 0.5. Following the multiplication of each prime angular view by the interpolation factor 314, the angular views within each subset are summed at 316. The sum of each subset is then used to generate the set of pseudo-angular views 318. The set of pseudo-angular views operate as a second set of angular views that are combined with the first set of angular views to form a final set of angular views that are used to reconstruct an image of the scan subject as discussed previously with particular reference to steps 216–220 of FIG. 7.

The present invention is illustrated in the following example. Assume for illustration purposes, a standard sampling condition for acquiring medical imaging data utilizes a sampling scheme with one second gantry rotation speed and a 1,000 Hz data sampling rate to acquire 1,000 angular views during one complete gantry rotation. Pursuant to one embodiment of the present invention, a sampling rate and a tube current may be reduced to reduce radiation dosage to the patient. That is, the sampling rate may be reduced from 1,000 Hz to 500 Hz and the tube current may be reduced by half. As a result, half (500) of the angular views are acquired as compared with the normal sampling rate scheme after one full rotation. Since the integration time has doubled, the counts for each of the 500 angular views may be maintained even though the tube current has been reduced by half. Five hundred pseudo-views are then created as described with reference to FIGS. 6 and 7 to create 1,000 total views. The 1,000 total views are then used to reconstruct an aliasing-free image of the scan subject.

In another example illustrating an alternative embodiment of the present invention, the sampling rate is maintained at 1,000 Hz, but the tube count is reduced by half. Accordingly, half of the number of standard angular views are then acquired. Prior to reconstruction of an image, every two adjacent views are added together to reduce the projection noise. Therefrom, 500 pseudo-views are created by interpolating between views to maintain 1,000 total views for image reconstruction. Depending upon the particular clinical application, radiation dosage may be reduced by 50% or more while also producing acceptable diagnostic images.

Therefore, in accordance with one embodiment of the present invention, a method prescribing a low dose scan of a subject to be scanned includes the steps of receiving a user input to lower tube current and acquiring a first set of angular views of the subject. The method further includes the steps of interpolating between each view of the first set of angular views and generating a second set of angular views therefrom. The method also includes the step of reconstructing an image of the subject from the first set and the second set of angular views.

In accordance with a further embodiment of the present invention, a computer readable storage medium having a computer program stored thereon is also provided. The computer program represents a set of instructions that when executed by a computer causes the computer to reduce the tube current of a CT imaging apparatus used to acquire imaging projections of a subject. The set of instructions further causes the computer to acquire a set of imaging projections corresponding to a set of angular views of the subject. The computer program then causes the computer to determine a set of pseudo-angular views from the set of imaging projections. The set of instructions then cause the computer to combine the set of angular views and the set of pseudo-angular views into a final set of angular views. The computer is then caused to reconstruct an image of the subject from the final set of angular views.

In accordance with yet another embodiment of the present invention, a CT system includes a rotatable gantry having an opening therein to receive a subject and a high frequency electromagnetic energy projection source configured to project high frequency electromagnetic energy to the subject. The CT system further includes a detector array configured to detect high frequency electromagnetic energy attenuated by the subject and generate a plurality of electrical signals indicative of the high frequency electromagnetic energy detected. The CT system further includes a computer connected to the detector array and programmed to acquire a set of projections from at least one region of the subject as well as determine a first set of views of the at least one region of the subject from the set of projections. The computer is also programmed to generate a second set of views from the first set of views and reconstruct an image of the at least one region of the subject from the first set and second set of views.

In accordance with yet another embodiment of the present invention, a CT system is provided and includes means for acquiring a set of projection data from a set of angular views of a subject as well as means for generating a set of pseudo-angular views from the set of angular views. The CT system further includes a means for forming a final set of angular views from the set of angular views and set of pseudo-angular views as well as a means for reconstructing images of the subject from the final set of angular views.

The present invention has been described in terms of the preferred embodiment, and it is recognized that equivalents, alternatives, and modifications, aside from those expressly stated, are possible and within the scope of the appending claims.

What is claimed is:

1. A method for prescribing a low dose scan of a subject to be scanned comprising the steps of:
   receiving a user input to lower tube current;
   acquiring a first set of angular views of the subject;
   interpolating between each view of the first set of angular views and generating a second set of angular views therefrom; and
   reconstructing an image of the subject from the first set and the second set of angular views.

2. The method of claim 1 further comprising the step of receiving a user input to reduce sampling rate for acquisition of the first set of angular views.

3. The method of claim 1 wherein the first set of angular views includes a plurality of data projections and wherein the step of generating includes averaging the data projection for a first angular view and the data projection for a second angular view of the first set of angular views to generate a first prime angular view and averaging the data projection for a third angular view and the data projection for a fourth angular view to generate a second prime angular view.

4. The method of claim 3 further comprising the step of summing half of the first prime angular view and half of the second prime angular view to generate the first angular view of the second set of angular views.

5. The method of claim 1 wherein the first set and the second set of angular views have an equal number of angular views.

6. The method of claim 1 wherein the subject includes a pediatric medical patient.

7. The method of claim 1 wherein the subject includes relatively small and centralized anatomical regions of a medical patient.

8. The method of claim 7 wherein the anatomical regions include at least one of a head and a heart.

9. A computer readable storage medium having a computer program stored thereon and representing a set of instructions that when executed by a computer causes the computer to:
   reduce tube current of a CT imaging apparatus used to acquire imaging projections of a subject;
   acquire a set of imaging projections corresponding to a set of angular views of the subject;
   determine a set of pseudo-angular views from the set of imaging projections;
   combine the set of angular views and the set of pseudo-angular views into a final set of angular views; and
   reconstruct an image of the subject from the final set of angular views.

10. The computer readable storage medium of claim 9 wherein the set of instructions further causes the computer to reduce data acquisition sampling rate for sampling the set of imaging projections.

11. The computer readable storage medium of claim 9 wherein the set of instructions further causes the computer to acquire the set of imaging projections with reduced radiation dosage.

12. The computer readable storage medium of claim 9 wherein the set of instructions further causes the computer to:
   (A) interpolate between projections of a first angular view, $\alpha_1$, and a second angular view, $\alpha_2$, of the first set of angular views; and
   (B) generate a first prime angular view, $\alpha'_1$; from the interpolation.

13. The computer readable storage medium of claim 12 wherein the set of instructions further causes the computer to repeat (A) and (B) for $\alpha_i, \alpha_{i+1}, \alpha_{i+2}, \ldots \alpha_N$ to generate $\alpha'_{i+1}, \alpha'_{i+2}, \alpha' \ldots, \alpha'_N$.

14. The computer readable storage medium of claim 13 wherein the set of instructions further causes the computer to:
   (C) multiply the first prime angular view, $\alpha'_i$, by 0.5;
   (D) multiply the second prime angular view, $\alpha'_2$, by 0.5; and
   (E) sum the product of (C) and (D) to generate a first pseudo-angular view, $p_1$.

15. The computer readable storage medium of claim 14 wherein the set of instructions further causes the computer to repeat (C)–(E) for remaining prime angular views, $\alpha'_N$, to generate pseudo-angular views $p_{i+1}, P_{i+2}, \ldots p_N$, of the set of pseudo-angular views.

16. A CT system comprising:
   a rotatable gantry having an opening therein to receive a subject;
   an HF electromagnetic energy projection source configured to project HF electromagnetic energy to the subject;
   a detector array configured to detect HF electromagnetic energy passing through the subject and generate electrical signals indicative of the HF electromagnetic energy detected; and
   a computer connected to the detector array and programmed to:

acquire a set of projections from at least one region of the subject;

determine a first set of views of the at least one region of the subject from the set of projections;

generate a second set of views from the first set of views;

reconstruct an image of the at least one region of the subject from the first set and the second set of views.

17. The CT system of claim 16 wherein the computer is further programmed to:

reduce tube current and data acquisition sampling rate;

segment the first set of views into a number of subsets;

average the views of each subset to generate a number of prime angular views; and interpolate between the number of prime angular views to generate the second set of views.

18. The CT system of claim 17 wherein the computer is further programmed to:

arrange the set of prime angular views into a number of subsets of prime angular views;

multiply each prime angular view of each subset of prime angular views by an interpolation factor; and thereafter, sum each subset of prime angular views.

19. The CT system of claim 18 wherein each subset of prime angular views includes at least two prime angular views and wherein the interpolation factor includes 0.5.

20. A CT system comprising:

means for acquiring a set of projection data for a set of angular views of a subject;

means for generating a set of pseudo-angular views from the set of angular views;

means for forming a final set of angular views from the set of angular views and the set of pseudo-angular views; and means for reconstructing an image of the subject from the final set of angular views.

* * * * *

UNITED STATES PATENT AND TRADEMARK OFFICE
CERTIFICATE OF CORRECTION

PATENT NO. : 6,459,755 B1  Page 1 of 1
DATED : October 1, 2002
INVENTOR(S) : Jianying Li It is certified that error appears in the above-identified patent and that said Letters Patent is hereby corrected as shown below:

<u>Column 8,</u>
Line 41, insert -- $\alpha'_i$ -- at the beginning of the line before "$\alpha'_{i+1}$".

Signed and Sealed this

Seventh Day of January, 2003

JAMES E. ROGAN
*Director of the United States Patent and Trademark Office*